United States Patent
Ross et al.

(10) Patent No.: US 8,415,630 B2
(45) Date of Patent: Apr. 9, 2013

(54) APPARATUS AND METHODS FOR DETERMINING A BOUNDARY OF AN OBJECT FOR POSITRON EMISSION TOMOGRAPHY SCATTER CORRECTION

(75) Inventors: Steven Gerard Ross, Pewaukee, WI (US); Timothy Wayne Deller, Pewaukee, WI (US); Ravindra Mohan Manjeshwar, Glenville, NY (US); Scott David Wollenweber, Waukesha, WI (US); Charles William Stearns, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 770 days.

(21) Appl. No.: 12/643,735

(22) Filed: Dec. 21, 2009

(65) Prior Publication Data

US 2011/0150306 A1    Jun. 23, 2011

(51) Int. Cl.
*G01T 1/161* (2006.01)
*G01T 1/166* (2006.01)
*A61B 6/00* (2006.01)

(52) U.S. Cl. .......... 250/363.02; 250/363.04; 378/7

(58) Field of Classification Search ............ 250/363.02–363.04, 252.1; 378/7; 382/131
See application file for complete search history.

(56) References Cited

U.S. PATENT DOCUMENTS

| | | | |
|---|---|---|---|
| 6,256,367 B1 * | 7/2001 | Vartanian | 378/7 |
| 6,490,476 B1 | 12/2002 | Townsend et al. | |
| 6,631,284 B2 | 10/2003 | Nutt et al. | |
| 6,740,883 B1 * | 5/2004 | Stodilka et al. | 250/363.04 |
| 7,312,455 B2 * | 12/2007 | Manjeshwar et al. | 250/363.03 |
| 8,017,914 B2 * | 9/2011 | Wollenweber et al. | 250/363.04 |

OTHER PUBLICATIONS

Charles C. Watson, Extension of Single Scatter Simulation to Scatter Correction of Time-of-Flight PET, IEEE Transactions on Nuclear Science, vol. 54, No. 5, Oct. 2007, pp. 1679-1686.
S.D. Wollenweber, Parameterization of a Model-Based 3-D PET Scatter Correction, IEEE Transactions on Nuclear Science, vol. 49, No. 3, Jun. 2002, pp. 722-727.
C.H. Holdsworth, et al., Performance Analysis of an Improved 3-D PET Monte Carlo Simulation and Scatter Correction, IEEE Transactions on Nuclear Science, vol. 49, No. 1, Feb. 2002, pp. 83-89.
C.H. Holdsworth, et al., Investigation of Accelerated Monte Carlo Techniques for PET Simulation and 3D PET Scatter Correction, IEEE Transactions on Nuclear Science, vol. 48, No. 1, Feb. 2001, pp. 74-81.

* cited by examiner

*Primary Examiner* — Alexander H Taningco
(74) *Attorney, Agent, or Firm* — The Small Patent Law Group; Dean D. Small

(57) ABSTRACT

Apparatus and methods for determining a boundary of an object for positron emission tomography (PET) scatter correction are provided. One method includes obtaining positron emission tomography (PET) data and computed tomography (CT) data for an object. The PET data and CT data is acquired from an imaging system. The method further includes determining a PET data boundary of the object based on the PET data and determining a CT data boundary of the object based on the CT data. The method further includes determining a combined boundary for PET scatter correction. The combined boundary encompasses the PET data boundary and the CT data boundary.

20 Claims, 7 Drawing Sheets

APPARATUS AND METHODS FOR DETERMINING A BOUNDARY OF AN OBJECT FOR POSITRON EMISSION TOMOGRAPHY SCATTER CORRECTION

BACKGROUND OF THE INVENTION

The subject matter disclosed herein relates generally to diagnostic imaging systems, and more particularly to positron emission tomography (PET) diagnostic imaging systems and correction of emission scatter.

PET imaging systems typically generate images depicting the distribution of positron-emitting nuclides in patients. The positron interacts with an electron in the body of the patient by annihilation, with the electron-positron pair converted into two photons. The photons are emitted in opposite directions along a line of response. The annihilation photons are detected by detectors (that are typically in a detector ring assembly) on both sides of the line of response on the detector ring assembly. These detections are termed coincidence events. The coincidence events detected by the PET detector ring assembly are typically stored within data structures called emission sinograms, which is a histogram of the detected coincidence events. An image of the activity distribution within a patient's body is generated from the emission sinograms through a process called image reconstruction.

Some photons are deflected from their original direction and such events are termed scatter events or scattered coincidences. It is desirable to reject the scatter events during the acquisition of emission sinograms, because images generated using only the detected true coincidence events represent a true activity distribution of radio-activity in the scanned body part of the patient. The deflected photons have less energy than the undeflected photons that comprise true coincidence events, and therefore scatter events can be rejected if one or both detected photons have measured energy substantially less than the 511 keV characteristic of undeflected photons. However, the energy measurement process for the detected photons is not perfect and some scatter events are incorrectly accepted as true coincidence events. The image reconstruction process must account for these detected scatter events in order for the PET imaging system to produce unbiased estimates of the activity distribution in the patient.

In conventional PET imaging systems, such as PET/computed tomography (PET/CT) imaging systems, three-dimensional (3D) PET model based scatter estimates are used to correct for the effects of photon scatter. The model based algorithms of these conventional systems estimate the shape of a scattered photon distribution in PET data. The shape is then adjusted to an accurate scaling level by comparing the magnitude of the model based estimate and the measured PET data outside the patient's body. For a PET scan, this method may be used because all of the sources are typically inside the body. In a PET/CT system, CT images or sinogram data can be used to estimate the boundary of the patient.

These methods, however, are sensitive to misregistration between the CT and PET data. Accordingly, if a patient moves, for example, moves a hand, arm or head, between the CT and PET portions of the PET/CT exam, valid photon count data may be interpreted as scatter because the conventional methods do not necessarily provide a proper scaled version of the scatter estimate. That is, a region of the PET sinogram that is assumed to have only scattered events, because the region is outside of the patient as determined by the CT imaging, also includes true PET emission events. These true emission events are then used to scale the scatter estimate, thus resulting in overscaling, and accordingly an overestimate of scatter.

BRIEF DESCRIPTION OF THE INVENTION

In accordance with various embodiments, a method for determining a boundary of an object for positron emission tomography (PET) scatter estimation is provided. The method includes obtaining positron emission tomography (PET) data and computed tomography (CT) data for an object. The PET data and CT data is acquired from an imaging system. The method further includes determining a PET data boundary of the object based on the PET data and determining a CT data boundary of the object based on the CT data. The method further includes determining a combined boundary for PET scatter correction. The combined boundary encompasses the PET data boundary and the CT data boundary.

In accordance with other embodiments, a computer readable medium for determining an image boundary is provided. The computer readable medium is programmed to instruct a computer to obtain positron emission tomography (PET) data and computed tomography (CT) data for an object, wherein the PET data and CT data is acquired from an imaging system. The computer readable medium is further programmed to instruct the computer to determine a PET data boundary of the object based on the PET data and determine a CT data boundary of the object based on the CT data. The computer readable medium is also programmed to instruct the computer to determine a combined boundary for PET scatter correction, wherein the combined boundary encompasses the PET data boundary and the CT data boundary.

In accordance with yet other embodiments, a positron emission tomography/computed tomography (PET/CT) dual imaging system is provided that includes a gantry and a plurality of imaging detectors coupled to the gantry for imaging an object. The PET/CT imaging system further includes acquisition circuitry for acquiring PET emission data and CT transmission data using the plurality of imaging detectors. The PET/CT imaging system also includes a scatter correction estimator module configured to determine a PET data boundary of the object based on the PET emission data, determine a CT data boundary of the object based on the CT transmission data and determine a combined boundary for PET scatter correction, wherein the combined boundary encompasses the PET data boundary and the CT data boundary.

DETAILED DESCRIPTION OF THE INVENTION

Figure 1:
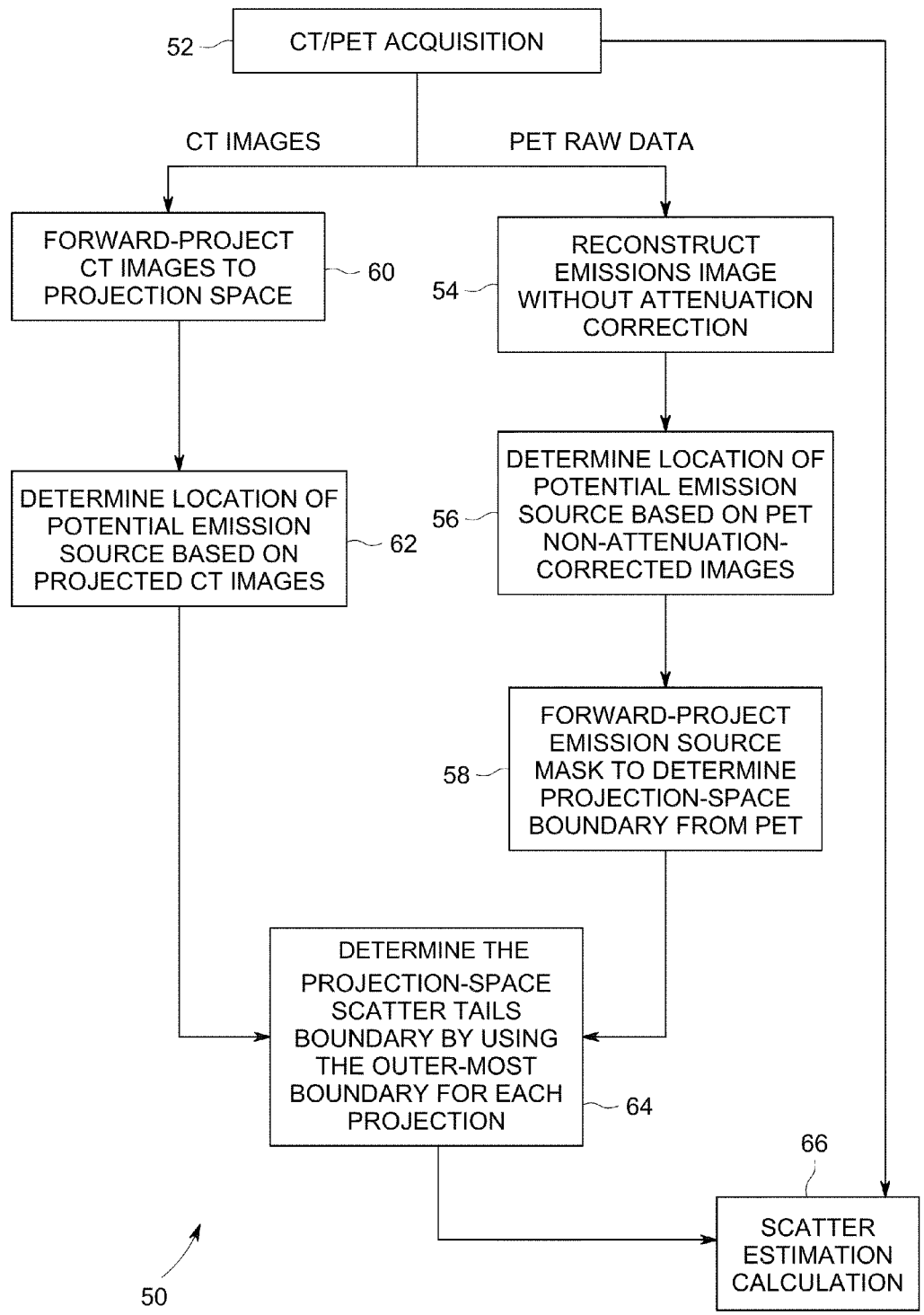
FIG. 1 is a flowchart of a method for determining an image boundary in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments use both computed tomography (CT) data sets (e.g., x-ray CT data) and positron emission tomography (PET) data sets to determine the boundary of an object, such as a patient. In the various embodiments, the outermost boundary from both of the data sets is then used to determine the effective boundary of the patient. A technical effect of various embodiments includes reducing or eliminating the overestimate of scattered events from misregistered CT/PET data determined from emission data within the effective boundary, which reduces image artifacts. Additionally, the robustness of PET scatter estimation for misregistered CT/PET data is improved. The various embodiments are also less sensitive to patient motion.

The various embodiments are implemented in connection with multi-modality imaging systems, for example, a PET/CT imaging system. However, it should be appreciated that although the various embodiments are described in connection with a PET/CT imaging system having a particular configuration, the various embodiments may be implemented in connection with PET/CT imaging systems have different configurations and components, as well as with other types of dual-modality imaging systems, for example, a single photon emission computed tomography (SPECT)/CT imaging system. Other modalities may be used, for example, an ultrasound system, Magnetic Resonance Imaging (MRI) or any other system capable of generating physiological activity distribution images or tomographic images. Moreover, the imaging detectors may be of different types and configurations. Also, although the various embodiments are described in connection with a multi-modality imaging system, the various embodiments may be implemented in a single modality imaging system.

Figure 2:
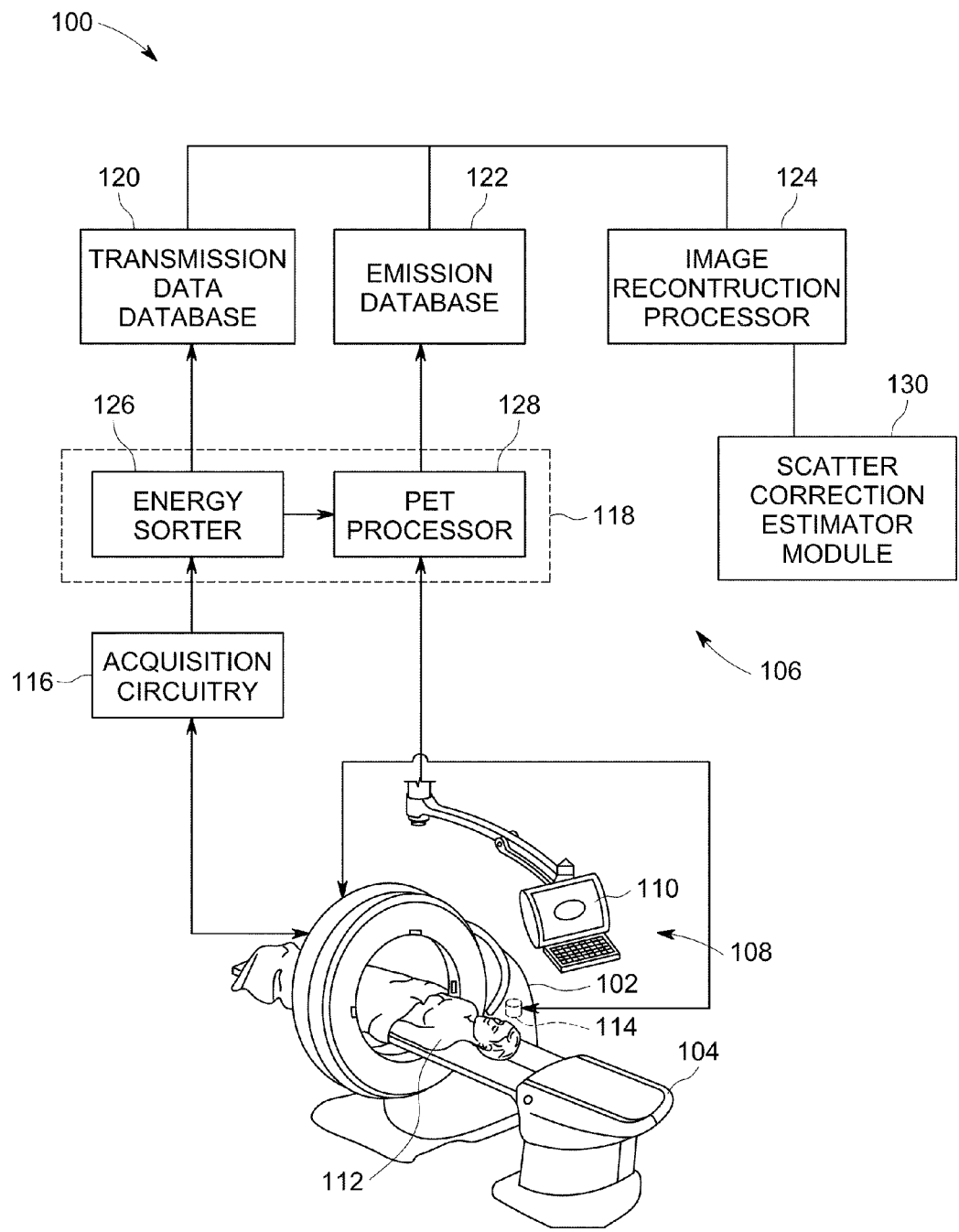
FIG. 2 is a schematic block diagram illustrating a positron emission tomography/computed tomography (PET/CT) dual imaging system formed in accordance with various embodiments.

In accordance with various embodiments, a method 50 for determining an imaging boundary, for example, the boundary of a patient is provided, which may be used to determine the emission data for use in PET scatter estimation. The method 50 includes obtaining image data at 52, which may be obtained from a CT/PET acquisition. For example, in a PET/CT imaging application, CT data (transmission data) from an x-ray CT scan and emission data from a PET scan and are both obtained. The acquisition of the data may include acquisition using a PET/CT imaging system 100 as illustrated in FIG. 2 or obtaining stored PET or x-ray CT data previously acquired by an imaging system. It should be noted that in some embodiments, the CT data is acquired prior to obtaining the PET data. However, the data may be acquired in different orders and combinations thereof (e.g., in an interleaved manner).

The medical imaging system, such as the PET/CT imaging system 100, generally includes a gantry 102, a patient table 104, and a processing and control system 106 including a user input 108 with a display 110. The gantry 102 provides mechanical support for imaging devices such as, for example, detectors, scanners and transmitters that are used for scanning a patient 112. The gantry 102 houses imaging devices such as, for example, PET detectors or x-ray detectors. It should be noted that the PET system may be a stationary annular detector or optionally may include a pin source.

The imaging devices on the gantry 102 acquire image data by scanning the patient 112 lying on the patient table 104. Moving the patient table 104 enables the scanning of various portions of the patient 112. The patient table 104 lies along the axis of gantry 102, which is known as a viewing area along an examination axis and can be moved along this axis. The patient table 104 can be positioned at various axial positions along the axis. In some embodiments, gantry 102 includes a plurality of PET detectors that are fixed and spaced on gantry 102, which are positioned radially outward from the axis. In accordance with other embodiments, the gantry 102 includes a plurality of detectors that are rotatable about the axis. For CT imaging, a rotating detector and a source, for example, an x-ray tube 114 may be provided and optionally including a stationary detector ring for CT imaging may be provided. In other embodiments, a separate imaging gantry is provided for CT imaging.

The processing and control system 106 controls the positioning of the patient table 104, as well as receiving image data collected during scanning. In various embodiments, the processing and control system 106 controls the medical imaging system 100 to acquire both emission and transmission image data, for example, of a volume of interest. For example, annihilation events may be detected as emission data, as well as transmission data from signals transmitted by a transmission source, such as the x-ray tube 114, which pass through the volume of interest of the patient 112. The transmission signals may get attenuated when the signals pass through the volume of interest and the detectors may collect data that is attenuated after the transmission signals pass through the patient 112.

Various processors, sorters, and databases are used to acquire and manipulate emission and transmission data, which is used in accordance with various embodiments. The processors, sorters and databases of FIG. 2 include acquisition circuitry 116, an acquisition processor 118, a transmission data database 120, an emission database 122, and an image reconstruction processor 124. The acquisition processor 118 is programmed to acquire emission data, for example, in a list mode and a sinogram mode, as described in more detail below, and generate an image based on the emission data acquired in the list mode and/or the emission data acquired in the sinogram mode. Other computing components also may be included.

In some embodiments, an energy sorter 126 provides, for example, time, location, and energy data to a PET processor 128. The PET processor 128 generally uses the received data to identify pairs of data, also known as coincidence pairs, coincident pair lines and lines of response, corresponding to annihilation events that occurred inside the region of interest. After acquisition processor 118 identifies an annihilation event, the acquisition processor 118 updates data in the emission data database 122 to store information relating to the annihilation event. X-ray CT data is also stored in the transmission data database 120 based on transmission signals that pass through the patient 112 and are detected.

Thus, after an acquisition session has been completed and sets of transmission and emission data have been stored in databases 120 and 122, respectively, image reconstruction processor 124 accesses the data in the databases 120 and 122 and uses the accessed data to generate images that may be requested by a system operator. Additionally, the sets of transmission and emission data are used by a scatter correction estimator module 130 to estimate scatter for the emission data based on both the transmission and emission data as described in more detail herein in connection with the method 50.

Referring again to the method 50 of FIG. 1, the emission data is reconstructed at 54 without attenuation correction to form an emission image. The reconstruction of the emission data may be performed in any suitable different manner. For example, in various embodiments, the reconstruction of the emission data is performed using an iterative reconstruction algorithm such as an ordered subset expectation-maximization (OSEM) method without attenuation correction. The OSEM method reduces the noise level in the reconstructed emission image. Additionally, the OSEM method reduces or eliminates the influence from a potentially misregistered CT image.

Referring again to the method 50 of FIG. 1, thereafter the location of a potential emission source is determined at 56 based on the non-attenuation corrected images. The non-attenuation corrected images generally provide images with edges that are more enhanced than attenuation corrected images. Accordingly, a determination may be made for each pixel of the non-attenuation corrected images whether there is any emission activity corresponding to that pixel. The pixels may be marked as pixels including emission activity (e.g., marked with a "1") and pixels that do not include emission activity (e.g., marked with a "0"). The determination of whether there is emission activity may be based on, for example, a threshold number of emission photon counts.

Thereafter, the emission data wherein potential emission source locations have been identified at 56 is forward projected into projection or sinogram space at 58 to determine a projection space boundary. In various embodiments, the marking of the pixels at 56 defines an emission source mask that is forward projected. In some embodiments, the forward projection is from a Cartesian coordinate system to a cylindrical coordinate system.

Figure 3:
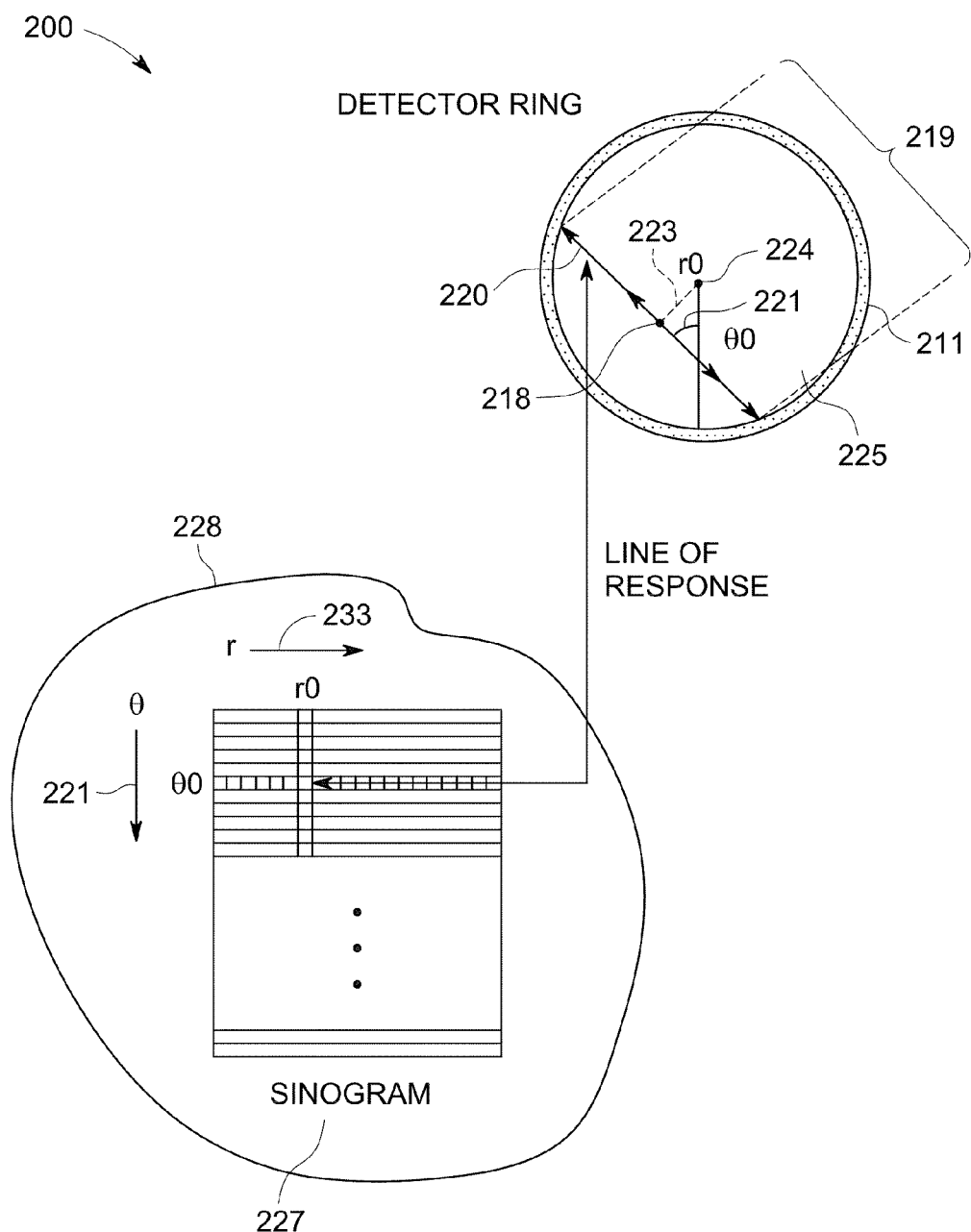
FIG. 3 is a diagram of a detector ring and an illustration of the construction of a sinogram used in various embodiments.

For example, FIG. 3 illustrates a perspective view 200 of a detector ring 211 and an illustration 228 of the construction of a forward projected data as a sinogram 227 formed in accordance with various embodiments. For example, energy sorter 126 (shown in FIG. 2) receives a coincidence event pair 219 of an annihilation event 218 and identifies a corresponding line of response 220. Each line of response 220 may be identified by an angle ($\theta$) 221 and a distance (r) 223 from a center 224 of the field of view 225. The array of the responses 220 is known as a sinogram 227, which may be stored as a two-dimensional (2D) or three-dimensional (3D) distribution. The sinogram 227, which is an emission sinogram, is essentially a histogram of detected coincidence events where each of a plurality of bins in the histogram represents a potential detector pair element. Accordingly, the data is forwarded projected from the x, y, z space to the r, $\theta$,z space.

The imaging system 100 includes multiple rings 211 of detectors covering, for example, 15-25 centimeters in the axial direction. Detectors typically include radiation detectors with sufficiently high timing resolution. The high timing resolution may be required to discriminate between at least two positions along the line of response 220 joining two such detectors. The photons are emitted in opposite directions along the line of response 220 and are detected by detectors placed on the line of response 220.

PET data may be acquired in either a 2D or 3D mode. In the 2D acquisition mode, lines of responses 220 occurring in the same ring 211 or immediately adjacent ring 211 are accepted. In the 3D mode, any line of response 220 occurring between any pair of detector rings 211 is acquired. In the 2D mode, the coincident events 219 that are acquired within the same detector ring 211 contribute to the direct planes, while those events 219 across neighboring rings 211 contribute to the cross planes.

Referring to the method 50 of FIG. 1, a projection space boundary from the PET emission data is also determined from the mask at 58, which may be the boundary of a volume of interest, for example, of a patient body, a portion of a patient body, etc. The boundary may be determined using any boundary detection or determination method. When using the mask, the boundary may be determined as the location where pixels change from marked as having emission activity to marked as having no emission activity, or vice versa. Continuing with the example above, the boundary may be determined when the marked value for the pixels changes from 1 to 0, or vice versa.

The various embodiments may use other methods for determining the boundary, for example, segmentation methods and/or thresholding to identify a boundary of the PET emission data. For example, segmentation methods may include region detection approaches that use thresholding, statistical analysis and/or clustering, and/or boundary detection methods that use thresholding and/or different models. For example, the boundary of the patient may be defined as the data points within the datasets having a value (e.g., coincidence count value) that is a percentage of a maximum value (e.g., fifteen percent of a maximum value). As another example, boundary detection may be performed by identifying edges in projection count profiles or spatial derivatives thereof.

In general, the boundary identification includes identifying an edge corresponding to the boundary of the patient, such as when the image data has a value change or a change that is greater than a predetermined amount (e.g., an abrupt change in count value). For example, segmentation of the foreground, where there is emission activity, from the background, where there is no emission activity (or minimal emission activity from scatter), is performed.

It should be noted that modifications and variations are contemplated. For example, different forms of the emission data may be used to determine the PET emission boundary of the patient (or a portion thereof). For example, the boundary may be determined from (1) the original PET emission data acquired by the PET imaging (sometimes referred to as raw data), (2) reconstructed OSEM emission images or (3) forwarded projected emission images. Thus, for example, the emission data may be forward projected vertically above a patient (starting from either end, namely a head or foot, of the patient) and the boundary determined by moving pixel by pixel until a threshold is exceeded or a mask value changes as described in more detail herein.

Referring again to the method of 50, the CT images, which in various embodiments is a stack of 2D images that form a 3D image, are forward projected at 60 from the image space into the projection space (also referred to as the sinogram space). The forward projection process for forward projecting the CT data may be performed in a similar manner to the forward projection process as described above with respect to the forward projection of the PET data at 54.

Thereafter, a location of a potential emission source activity is determined based on the forward projected CT images at 62. For example, the boundary of the patient (or a portion thereof) is determined from the CT data at 62. The process for identifying the boundary using the CT data is performed similar to methods described above in connection with boundary detection using the emission data. In general, any suitable method for detecting a border, such as segmentation methods to identify the patient boundary may be used, which uses, for example, the CT values for each of the pixels or voxels in the CT image. In various embodiments, the boundary determination may be performed using CT sinogram data or CT image data.

Figure 4:
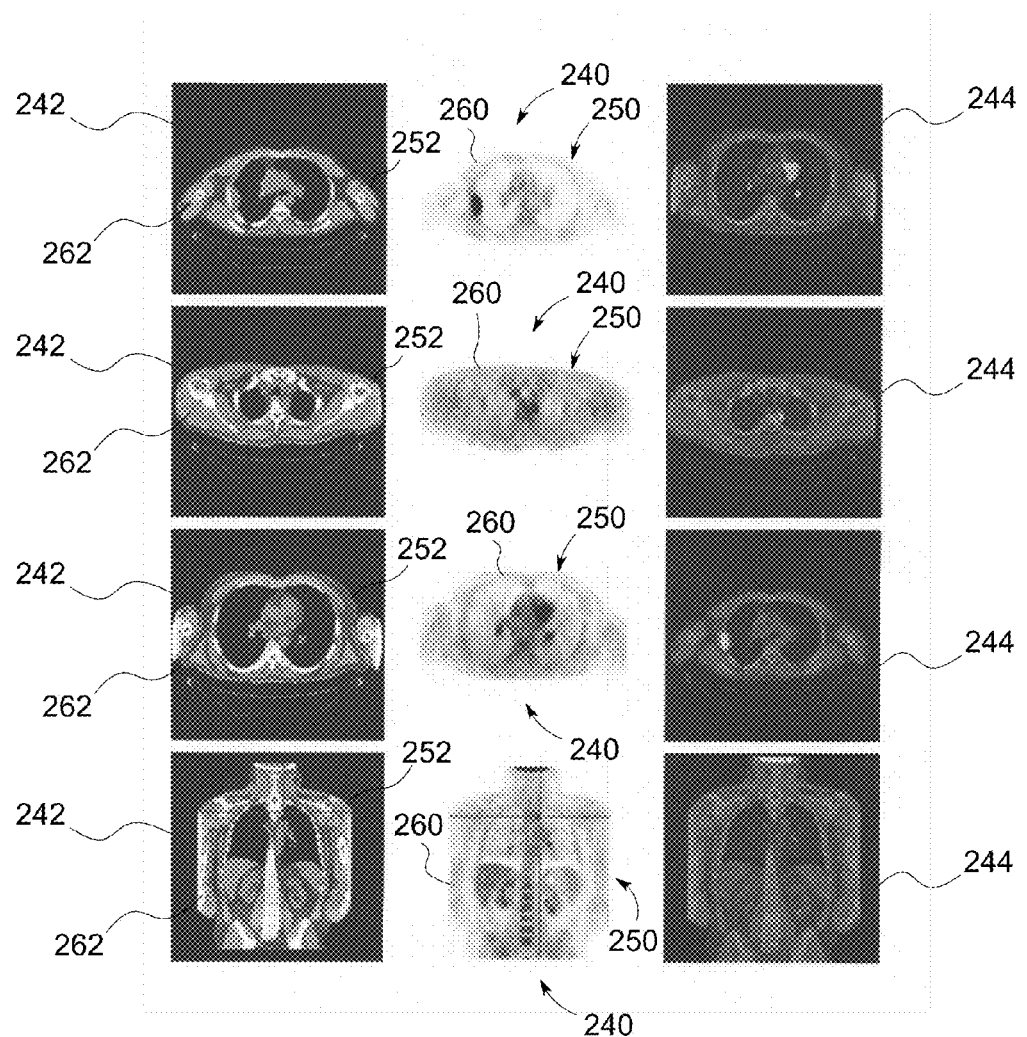
FIG. 4 are images acquired by the PET/CT dual imaging system of FIG. 2 illustrating boundary determination in accordance with various embodiments.

Thus, as shown in FIG. 4, illustrating PET images 240 and CT images 242 that may be reconstructed using the PET emission and x-ray CT data as described in more detail herein, a boundary 250 of the patient (or portion of the patient) is identified using the emission data and a boundary 242 of the patient (or portion of the patient) is identified using the x-ray CT data.

Referring again to the method 50 of FIG. 1, the outer limit of the boundary based on both data sets is determined at 64. In particular, a projection-space scatter tails boundary is determined using the outermost boundary for each projection. The scatter tails are generally emission events occurring outside the combined boundary that may be caused, for example, from patient scatter. In various embodiments, a combined boundary that encompasses the PET data boundary and the CT data boundary may be identified as the outermost limit of the boundary from either the PET data or CT data for each projection or pixel. In some embodiments, the outermost data points are identified from both the emission data set and CT data set. In particular, for each boundary position or location, the extent of the boundary is defined as the outermost data point for that position or location based on the emission data or the CT data for that position or location.

Thus, if a particular position or location of the identified boundary is greater (e.g., wider) in the emission data set, then the emission data point is used to define the boundary at that position or location. If for a particular position or location of the identified boundary is greater (e.g., wider) in the CT data set, then the CT data point is used to define the boundary at that position or location. Thus, as shown in FIG. 4, for a corresponding point 260 and 262 of the boundary (and for every other determined point along the boundary), based on the emission image data and CT image data, respectively, a determination is made as to which point 260 or 262 is the outermost point, for example, to define the largest patient boundary.

It should be noted that in some embodiments a point by point comparison is not performed. Instead, the data set, namely the emission data set or the CT data set having the largest boundary, for example, based on circumference size or area, is used as the patient boundary.

Thereafter, and referring again to the method 50 of FIG. 1, at 66 the outermost sinogram boundary, based on the boundary determination at 62, is used to estimate scattered events. It should be noted that if the image is used instead of the sinogram to determine the boundary, the boundary is forward projected to map the boundary to the sinogram space.

The scatter estimation may be performed using any suitable method. The scatter estimation is performed using emission data within the determined boundary. For example, a scatter model may be used to perform scatter correction on the emission data set. The scatter correction model may perform scatter correction by identifying scatter coincidence events within the emission data set (defined by the boundary) to enable the true coincidence events to be used to reconstruct an image of the patient. The scatter correction model may also be embodied as a set of instructions or an algorithm performed, for example, by the scatter correction estimator module 130 (shown in FIG. 1). The scatter correction model may be a mathematical algorithm or a logical representation of the processes utilized to identify scatter coincidence events within the emission data set. The mathematical scatter correction model may utilize mathematical language to identify scatter coincidence events within the emission data set. The scatter correction model may also perform, among other things, normalization of the emission data set and attenuation correction of the emission data set.

In various embodiments, the scatter estimate is scaled using, for example, a comparison to the estimated data from the outer sinogram boundary. The scaling estimate may be performed using any suitable method. In some embodiments, the scaling of the scatter estimate is performed using one of a least square fit or a summation of events, or another data comparison method.

Accordingly, scatter corrected images 244 as shown in FIG. 4 may be generated and displayed. The images 244 are a fused and registered combination of the images 240 and 242. The images 240 and 242 may be combined using any suitable method.

It should be noted that the boundary determinations in the method 50 of FIG. 1 based on the PET data and the CT data may be performed in any order. Accordingly, although the method 50 is described as determining a boundary based on the PET data first (before the determination of the boundary based on the CT data), a boundary based on the CT data may be determined first. Optionally, the boundaries based on the PET data and the CT data may be determined in parallel.

Thus, in accordance with various embodiments, PET data is used to determine the boundary of a patient. For example, the various embodiments may use either the PET emission data directly, or use a forward projection of a PET image reconstructed without attenuation correction. The reprojected image generally results in lower noise than the original PET data, particularly if the reconstruction is performed with an iterative reconstruction algorithm as described herein. The boundary, for example, patient boundary is then created either directly on the PET non-attenuation corrected (NAC) image or on the PET NAC sinogram. A comparison is then performed, for example, between the PET NAC boundary and the CT boundary, and the greater of the two boundaries (which may be for each of a plurality of points) is used as the patient boundary.

Accordingly, during PET scatter correction, an estimate of the shape of the PET scatter profile can be obtained using a model based scatter estimation. This model based method is effective to obtain the overall shape of the scatter, however, the model alone does not necessarily provide a properly scaled version of the scatter estimate. To obtain the scaling for the scatter estimate, the edges of the body are determined from both the emission data and either the CT image or the CT sinogram. Accordingly, any data outside of the body is assumed to be from scatter. A comparison of the scatter estimate outside the body and the emission data outside the body can then be performed, which may include methods using sum of counts or least squares fit. Because it can be assumed that any emission activity outside the patient is scatter events (particularly since random events have been subtracted), the measured emission data can be used to scale the estimated scatter data.

Thus, various embodiments account for CT-PET misregistration where the outline or boundary of the patient in the CT image or sinogram does not match the outline in the PET image or sinogram, which may occur, for example, as a result of hand motion, head motion, or the spilling of activity outside the patient on low attenuating material, such as a gown. The various embodiments can account for these conditions or movements to provide improved scatter estimates.

Figure 5:
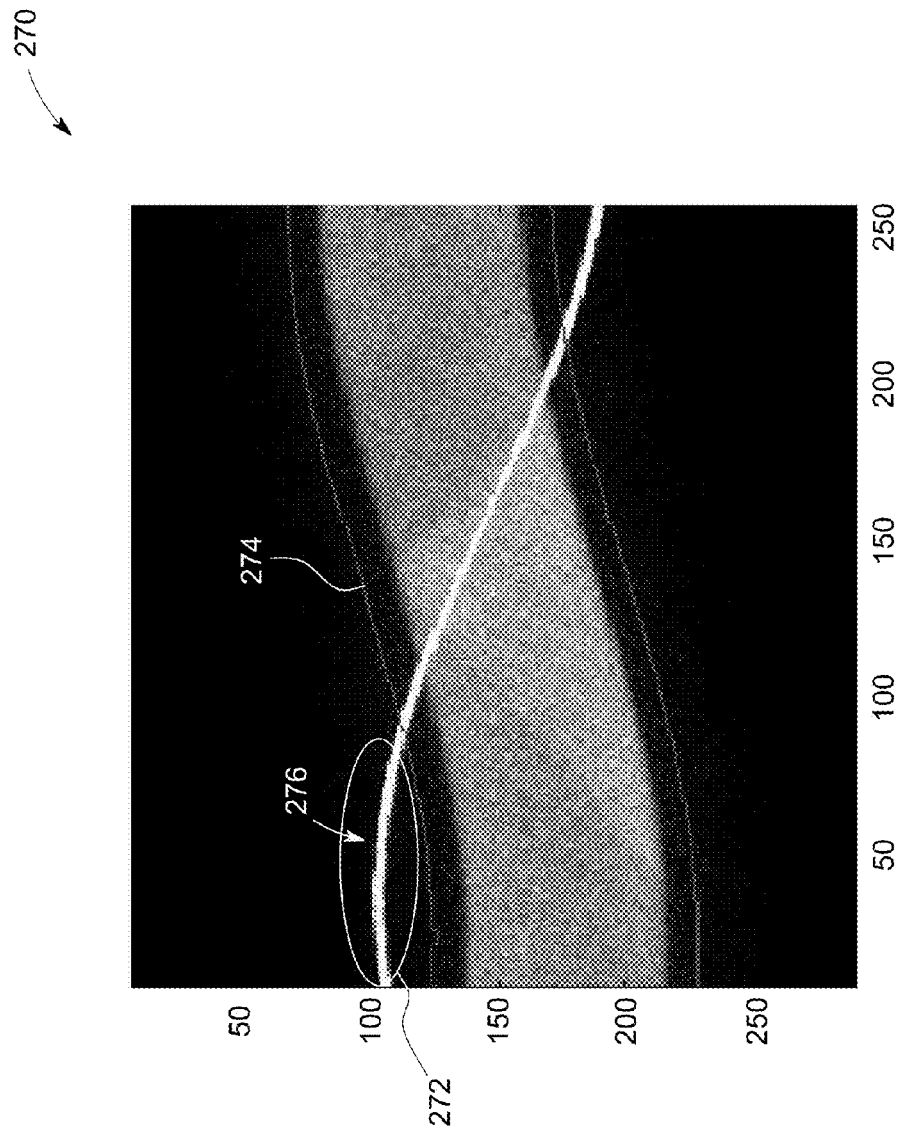
FIG. 5 is a sinogram image illustrating an incorrect boundary determined as a result of CT-PET misregistration.
Figure 6:
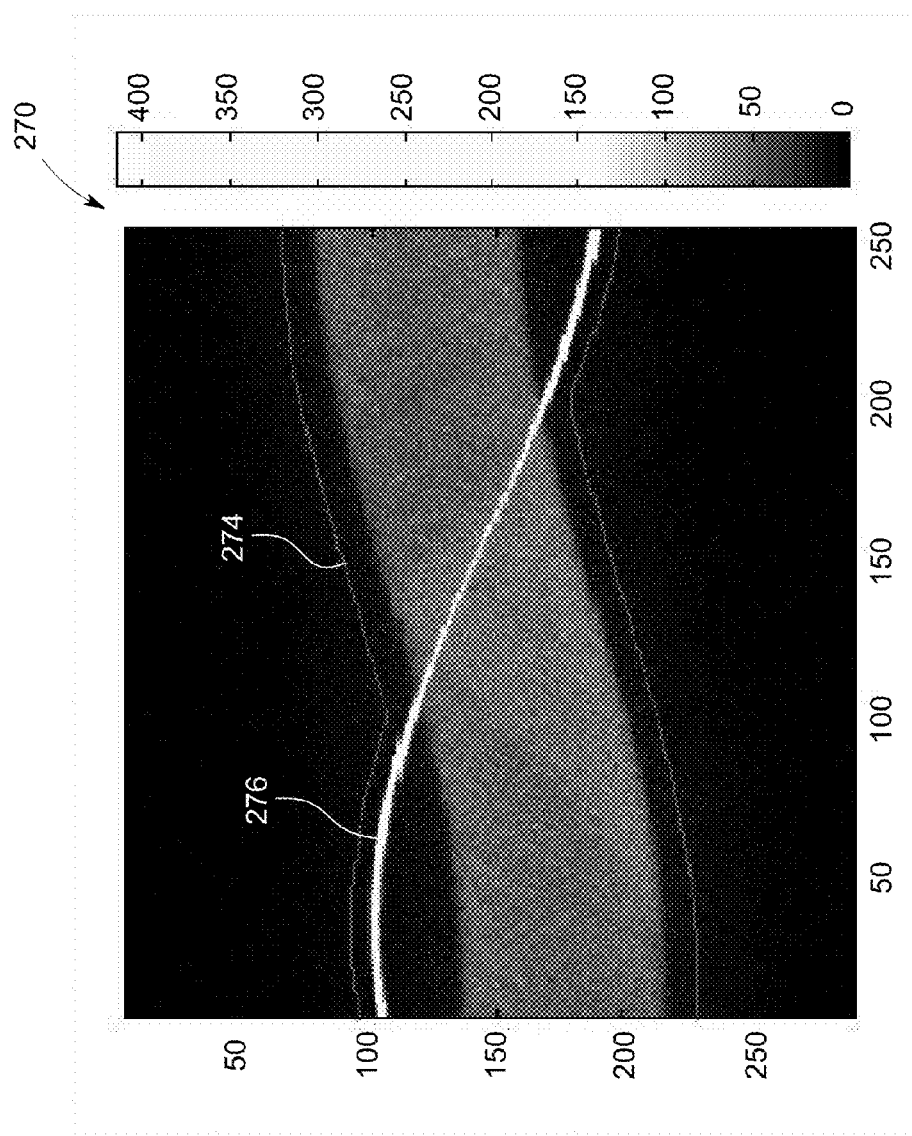
FIG. 6 is a sinogram image illustrating a boundary determined in accordance with various embodiments.

Thus, for example, a sinogram image 270 of FIG. 5, illustrates CT-PET misregistration using a phantom. In the sinogram image, the vertical axis represents the radial dimension and the horizontal axis represents the projection space (in degrees). As can been seen, emission activity, and in particular, true emission data 276 outside the boundary 274 defined by CT data, which is identified at 272, will be treated as scattered events, which will then be used to scale the scatter estimate. Accordingly, improper scaling will occur as a result of the determined boundary from the CT data. However, as shown in FIG. 6, the boundary 274 determined based on the various embodiments using both emission and CT data does not include true emission data 276 outside the boundary 274.

Figure 7:
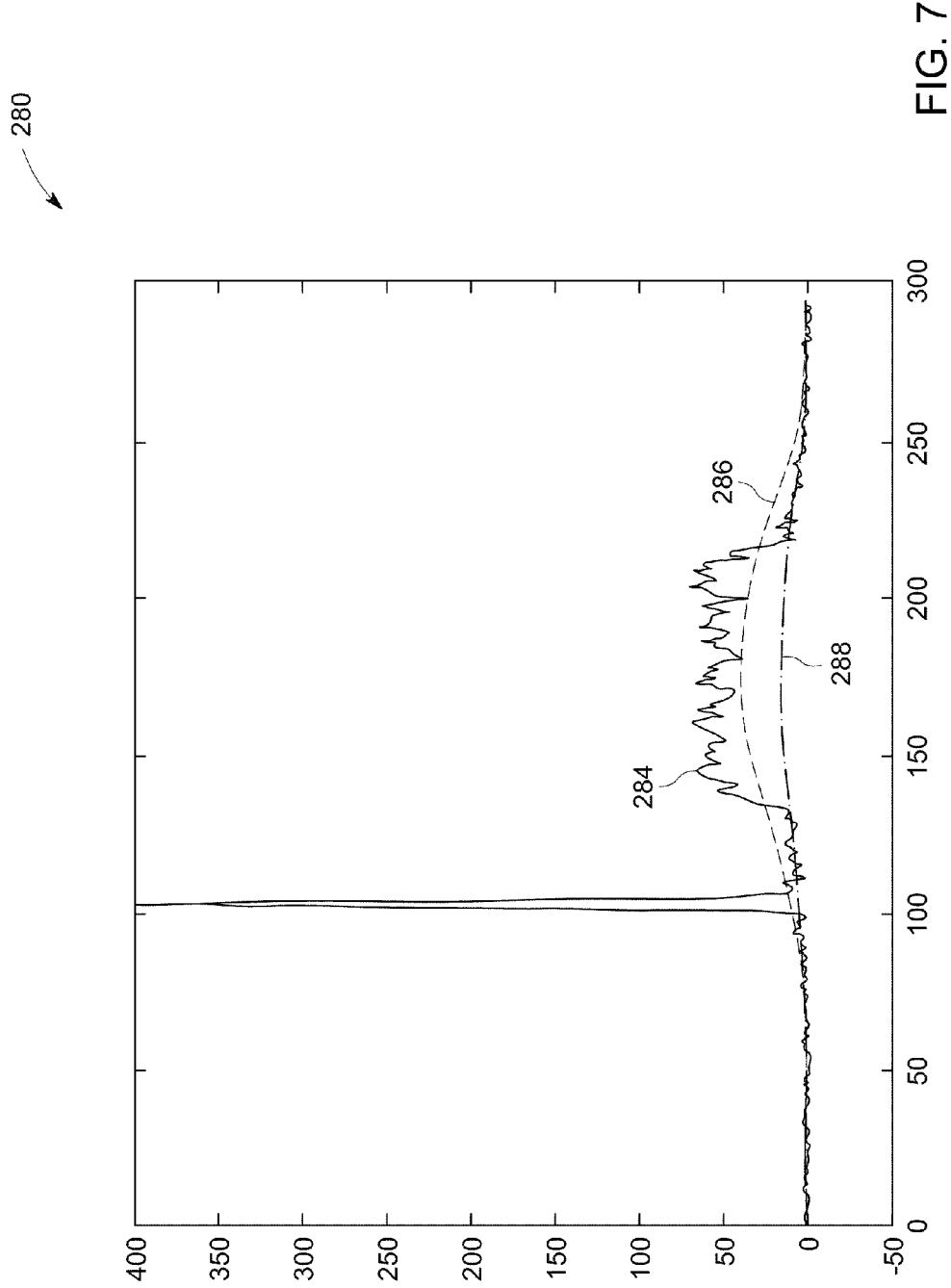
FIG. 7 is a graph illustrating profiles of emission data corresponding to different scatter estimates.

Moreover, FIG. 7 is a graph 280 illustrating profiles of emission data corresponding to scatter estimates. In the graph 280, the vertical axis represents amplitude corresponding to PET counts and the horizontal axis represents radial bins, for example, projection bins corresponding to points around a gantry. The curve 284 is a plot of the True+Scatter data. The curve 286 shows the scatter estimate obtained from misregistered CT data. The curve 288 is the scatter estimate from the registered CT data in accordance with various embodiments of the invention. As can be seen, the curve 286 provides an artificially high level of scatter estimate. This can be seen, for example, on the right side of the curve 286 that is outside a phantom region. In this area, the curve 284 is primarily scattered events. While the curve 288 follows the curve 284 closely, the curve 286 is much higher. Because this activity extends into the region of true activity, this will tend to wash out (over correct) emission image data.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for determining a boundary of an object for positron emission tomography (PET) scatter estimation, the method comprising:
    obtaining positron emission tomography (PET) data and computed tomography (CT) data for an object, the PET data and CT data acquired from an imaging system;
    determining a PET data boundary of the object based on the PET data;
    determining a CT data boundary of the object based on the CT data; and
    determining a combined boundary for PET scatter correction, the combined boundary encompassing the PET data boundary and the CT data boundary.

2. A method in accordance with claim 1 further comprising reconstructing the PET image data to generate an emission image using ordered subset expectation-maximization (OSEM) without attenuation correction and thereafter using the reconstructed emission image when determining the boundary.

3. A method in accordance with claim 1 further comprising forward projecting the PET image data into sinogram space to generate a forward projected emission image and using the forward projected emission image when determining the boundary.

4. A method in accordance with claim 1 wherein the PET image data comprises emission data from a PET imaging system.

5. A method in accordance with claim 1 wherein the CT image data comprises one of a CT sinogram and a CT image.

6. A method in accordance with claim 1 further comprising determining an outermost boundary from the PET image data and the CT image data, the outermost boundary defining the combined boundary.

7. A method in accordance with claim 6 wherein the outermost boundary is determined using forward projected non-attenuation corrected PET image data and forward projected CT image data.

8. A method in accordance with claim 1 further comprising estimating scattered events in an emission sinogram of the PET image data using the combined boundary.

9. A method in accordance with claim 8 further comprising scaling a scatter estimate using the estimated scattered events.

10. A method in accordance with claim 1 wherein determining a combined boundary comprises segmenting a foreground from a background in at least one of the PET image data and CT image data.

11. A method in accordance with claim 1 further comprising comparing an emission image generated from the PET image data and a CT image generated from the CT image data to determine the combined boundary.

12. A method in accordance with claim 11 wherein the object is a patient and further comprising using a larger of the boundary from the emission image and CT image to define a patient boundary.

13. A computer readable medium for determining an image boundary, the computer readable medium being programmed to instruct a computer to:
    obtain positron emission tomography (PET) data and computed tomography (CT) data for an object, the PET data and CT data acquired from an imaging system;
    determine a PET data boundary of the object based on the PET data;
    determine a CT data boundary of the object based on the CT data; and
    determine a combined boundary for PET scatter correction, the combined boundary encompassing the PET data boundary and the CT data boundary.

14. A computer readable medium in accordance with claim 13 wherein the PET image data comprises one of raw emission data, a forward projected emission image and reconstructed image data using ordered subset expectation-maximization (OSEM) with no attenuation correction.

15. A computer readable medium in accordance with claim 13 wherein the CT image data comprises one of a CT sinogram and a CT image.

16. A computer readable medium in accordance with claim 13 wherein the program further instructs the computer to determine an outer limit of each of a sinogram or image row in the PET image data and CT image data for use in determining the combined boundary.

17. A computer readable medium in accordance with claim 16 wherein the program further instructs the computer to estimate scattered events in a sinogram of PET image data using the determined combined limit.

18. A computer readable medium in accordance with claim 17 wherein the program further instructs the computer to scale the scatter estimate using a comparison to data from the outer limit sinogram determination.

19. A positron emission tomography/computed tomography (PET/CT) dual imaging system comprising:
    a gantry;
    a plurality of imaging detectors coupled to the gantry for imaging an object;
    acquisition circuitry for acquiring PET emission data and CT transmission data using the plurality of imaging detectors; and
    a scatter correction estimator module configured to determine a PET data boundary of the object based on the PET emission data, determine a CT data boundary of the object based on the CT transmission data and determine a combined boundary for PET scatter correction, wherein the combined boundary encompasses the PET data boundary and the CT data boundary.

20. A PET/CT dual imaging system in accordance with claim 19 wherein the scatter correction estimator module is further configured to compare a boundary determined from the PET emission data and the CT transmission data, and use an outermost boundary to estimate the scatter correction.

* * * * *